(12) United States Patent
Mothilal et al.

(10) Patent No.: US 7,591,185 B1
(45) Date of Patent: Sep. 22, 2009

(54) PRESSURE SENSOR CONFIGURATIONS FOR IMPLANTABLE MEDICAL ELECTRICAL LEADS

(75) Inventors: Kamal Deep Mothilal, Plymouth, MN (US); Michael A. Schugt, St. Paul, MN (US); David A. Ruben, Mesa, AZ (US); Jonathan P. Roberts, Coon Rapids, MN (US); Clark B. Norgaard, Phoenix, AZ (US); Lary R. Larson, Gold Canyon, AZ (US)

(73) Assignee: Medtronic, inc., Minneapolis, MN (US)

( * ) Notice: Subject to any disclaimer, the term of this patent is extended or adjusted under 35 U.S.C. 154(b) by 0 days.

(21) Appl. No.: 12/108,212

(22) Filed: Apr. 23, 2008

(51) Int. Cl.
*G01L 9/12* (2006.01)
*A61N 1/00* (2006.01)

(52) U.S. Cl. .............................. 73/718; 600/486; 607/17

(58) Field of Classification Search .................. 73/718, 73/724; 607/9.17, 122; 600/486
See application file for complete search history.

(56) References Cited

U.S. PATENT DOCUMENTS

| | | | |
|---|---|---|---|
| 5,554,176 A * | 9/1996 | Maddison et al. ............... | 607/9 |
| 5,639,989 A | 6/1997 | Higgins, III | |
| 5,755,766 A * | 5/1998 | Chastain et al. ............. | 607/122 |
| 6,221,024 B1 * | 4/2001 | Miesel ........................ | 600/486 |
| 6,453,749 B1 * | 9/2002 | Petrovic et al. ................ | 73/754 |
| 6,631,555 B1 | 10/2003 | Youker et al. | |
| 7,129,422 B2 | 10/2006 | Arnold | |
| 7,231,259 B2 | 6/2007 | Jenney et al. | |
| 7,231,829 B2 | 6/2007 | Schugt | |
| 2004/0020674 A1 | 2/2004 | McFadden et al. | |
| 2006/0064135 A1 * | 3/2006 | Brockway ..................... | 607/17 |
| 2006/0247539 A1 * | 11/2006 | Schugt et al. ................ | 600/486 |
| 2007/0107524 A1 | 5/2007 | O'Brien et al. | |
| 2007/0199385 A1 | 8/2007 | O'Brien et al. | |

\* cited by examiner

*Primary Examiner*—Andre J Allen
(74) *Attorney, Agent, or Firm*—Stephen W. Bauer; Michael J. Ostrom (57) ABSTRACT

An implantable pressure sensor, which may be incorporated within an implantable medical electrical lead, includes an insulative sidewall, which contains a gap capacitor and an integrated circuit. The insulative sidewall of the pressure sensor includes a pressure sensitive diaphragm portion, and the gap capacitor includes a first electrode plate, which is attached to an interior surface of the diaphragm portion of the sidewall, and a second electrode plate, which is spaced apart from the first electrode plate and coupled to the integrated circuit, which is coupled, through the sidewall, to a supply contact and a ground contact. A conductive layer extends over one of the interior surface of the diaphragm portion of the sidewall and an exterior surface of the diaphragm portion; and the conductive layer is coupled to the ground contact to either shield or ground the first electrode plate.

33 Claims, 10 Drawing Sheets

PRESSURE SENSOR CONFIGURATIONS FOR IMPLANTABLE MEDICAL ELECTRICAL LEADS

TECHNICAL FIELD

The present disclosure relates to implantable medical electrical leads and more particularly to pressure sensor configurations for the leads.

BACKGROUND

Implantable systems for cardiac rhythm management often employ medical electrical leads, which extend into the venous blood stream and couple a therapy delivery generator device to a surface of the heart. Typically, a medical electrical lead includes one or more electrodes for stimulating the heart and for sensing electrical activity of the heart.

In addition to, or in lieu of electrodes, a medical electrical lead may include one more other types of sensors, for example, a pressure sensor. An exemplary pressure sensor is a microelectromechanical systems (MEMS) capacitive pressure transducer. This type of pressure sensor typically includes a hermetically sealed capsule that contains a gap capacitor and an integrated circuit (IC) chip coupled thereto. Feedthroughs extend through a sidewall of the capsule to couple the IC chip to external contacts, source and ground, and the contacts are coupled to conductors extending within the lead body. Examples of this type of sensor are described United States pre-grant patent publications 2007/0107524 and 2007/0199385, which are hereby incorporated by reference in their entirety.

BRIEF DESCRIPTION OF THE DRAWINGS

The following drawings are illustrative of particular embodiments of the present disclosure and therefore do not limit the scope of the invention. The drawings are not to scale (unless so stated) and are intended for use in conjunction with the explanations in the following detailed description. Embodiments of the present disclosure will hereinafter be described in conjunction with the appended drawings, wherein like numerals denote like elements.

DETAILED DESCRIPTION

The following detailed description is exemplary in nature and is not intended to limit the scope, applicability, or configuration of the invention in any way. Rather, the following description provides practical illustrations for implementing exemplary embodiments of the present invention. Examples of constructions, materials, dimensions, and manufacturing processes are provided for selected elements, and all other elements employ that which is known to those of skill in the field of the invention. Those skilled in the art will recognize that many of the examples provided have suitable alternatives that can be utilized.

Electronic components, which are not shielded and/or grounded, may be susceptible to problems associated with electromagnetic interference (EMI), and implantable medical electrical leads may include such electronic components. The integration of shielding and/or grounding into an implantable medical electrical lead poses some unique design challenges. Embodiments of medical electrical leads, which are described herein, include a pressure sensor and one or more conductive coatings formed over a surface of at least one sidewall of the pressure sensor in order to shield and/or ground at least a capacitive pressure transducer contained within the sidewall of the pressure sensor.

Figure 1:
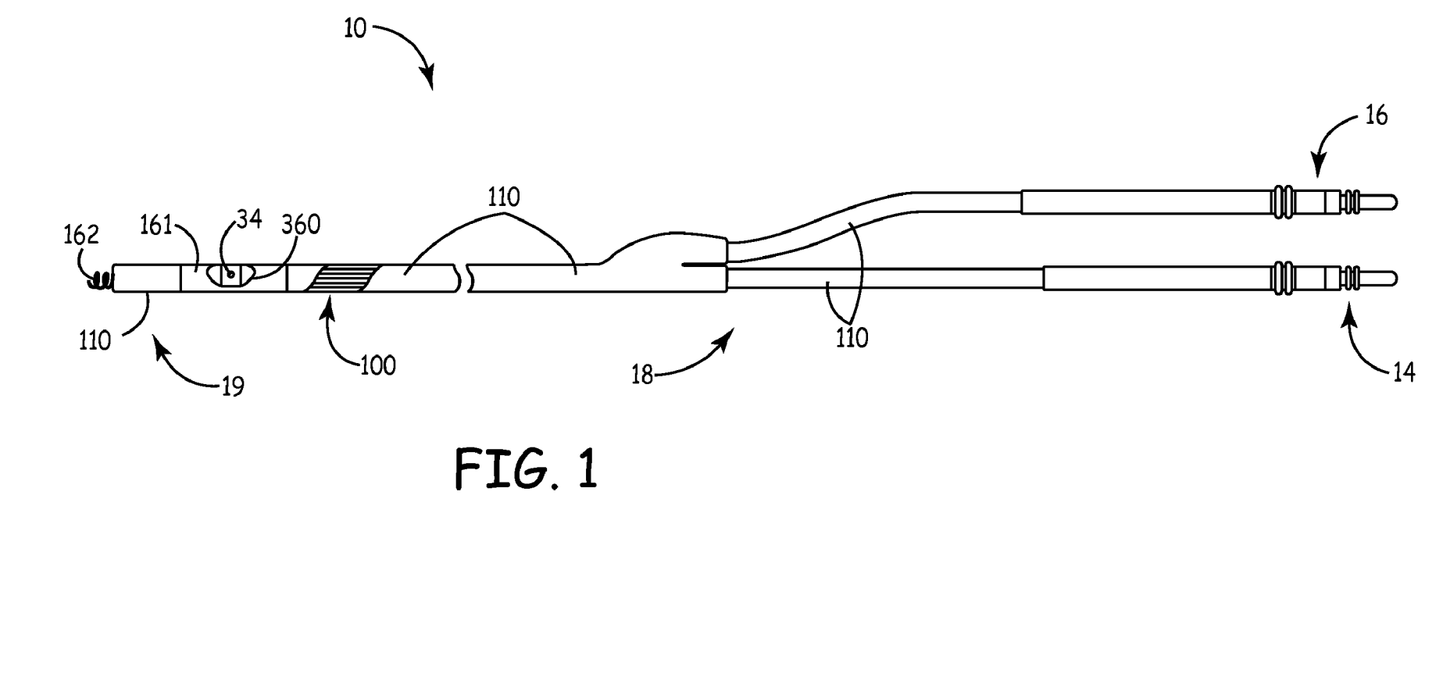
FIG. 1 is a plan view, with a cut-way portion, of medical electrical lead, according to one embodiment.
Figure 2:
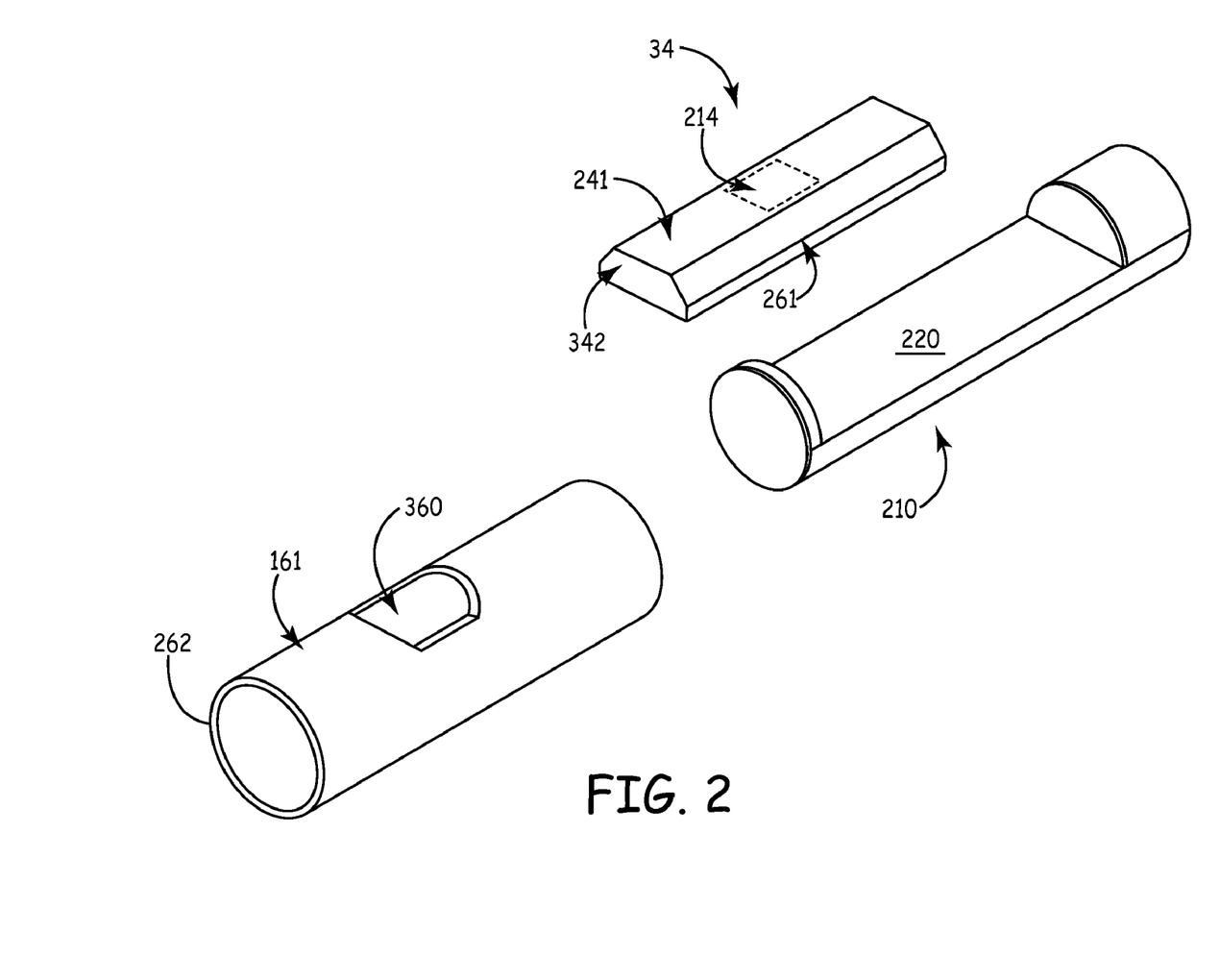
FIG. 2 is an exploded perspective view of a portion of the lead shown in FIG. 1.

FIG. 1 is a plan view of a medical electrical lead 10, according to one embodiment. FIG. 1 illustrates lead 10 including an insulative lead body 110, which is terminated at a proximal end 18 with a pair of connectors 14, 16 and is terminated at a distal end 19 by a tip electrode 162. According to the illustrated embodiment, a pressure sensor 34 is mounted to lead body 110, and another electrode 161 extends about pressure sensor 34. Electrode 161 includes an aperture 360, to expose a pressure sensitive diaphragm portion 214 of sensor 34, which is seen in the exploded perspective view of FIG. 2. FIG. 2 illustrates a platform portion 210 of lead body 110 including a mounting surface 220 on which sensor 34 is mounted, for example, being adhered thereto, via adhesive bonding. Portion 210 may be separately formed, for example, molded from a relatively rigid plastic, and adapted for integration into lead body 110. Although not shown in FIG. 2, platform 210 preferably includes conduits allowing for a plurality of conductors 100 to couple with pressure sensor 34 and electrodes 161, 162. Platform 210, sensor 34 and electrode 161 may be integrated into lead body 110, for example, as described in commonly-assigned and co-pending U.S. patent application Ser. No. 12/107,987, which is hereby incorporated by reference in its entirety. Pressure sensor 34 is preferably constructed according to microelectromechanical systems (MEMS) fabrication methods and includes a capacitive pressure transducer contained by a capsule, which is formed by an insulative sidewall 342, for example, a biocompatible ceramic, such as glass, fused silica, sapphire quartz or silicon. Insulative sidewall 342 is shown including a lid portion 241 and a base portion 261, wherein lid portion 241 includes pressure-sensitive diaphragm portion 214, and is attached to base portion 261, for example, via a laser fusing process, to form a sealed cavity, as is shown in FIGS. 3B-C.

Figure 3A:
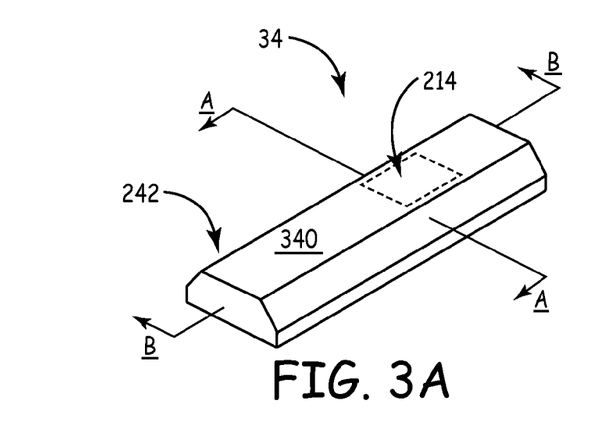
FIG. 3A is a perspective view of a pressure sensor, according to one embodiment.
Figure 3B:
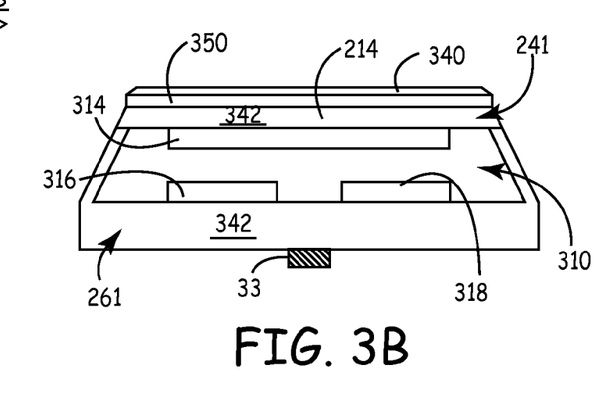
FIGS. 3B-C are section views, through section lines A-A and B-B, respectively, of FIG. 3A, according to some embodiments.
Figure 3C:
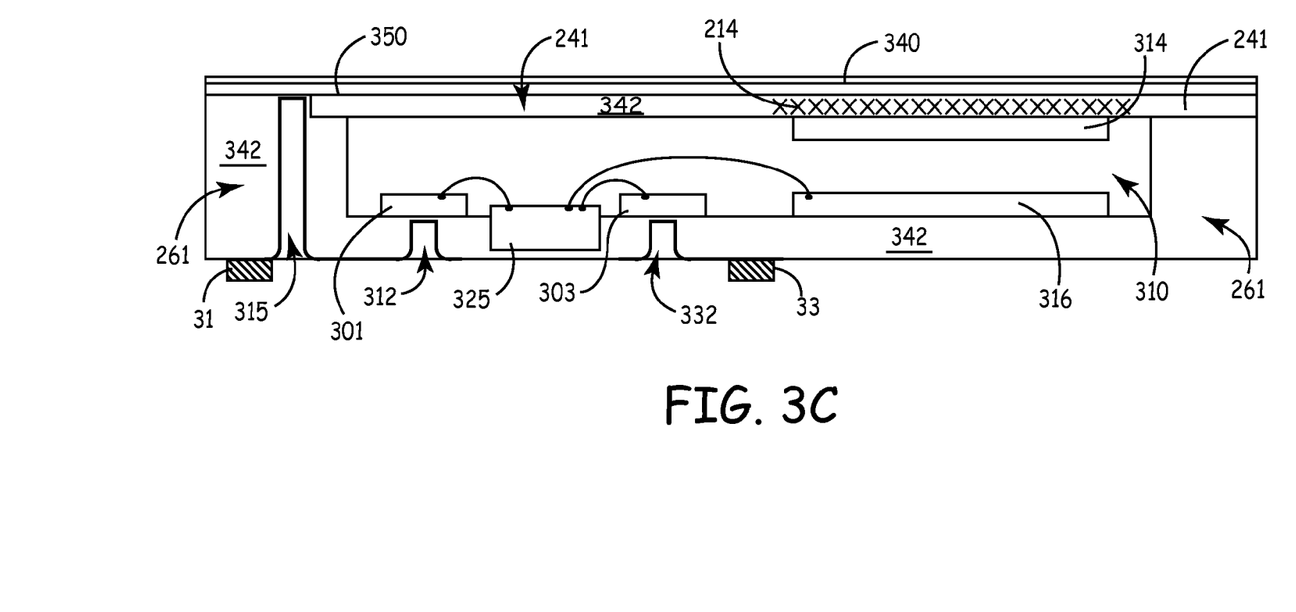

FIG. 3A is a perspective view of pressure sensor 34; and FIGS. 3B-C are section views, through section lines A-A and B-B, respectively, of FIG. 3A. FIGS. 3B-C illustrate a gap capacitor 310, which is contained by insulative sidewall 342, and which includes a first electrode plate 314 spaced apart from second and third electrode plates 316, 318, which are pick-off and ground, respectively. First electrode plate 314 is shown attached to an interior surface of diaphragm portion 214, so as to move with diaphragm portion 214, in response to external changes in pressure. Plates 316, 318, which are shown attached to an interior surface of base portion 261 of sidewall 342, remain fixed. FIG. 3C illustrates gap capacitor 310 coupled to an integrated circuit (IC) chip 325, which is coupled to conductive traces 301, 303. Conductive traces 301, 303 are, in turn, coupled, through insulative sidewall 342, to a ground contact 31 and to a supply contact 33, respectively, by corresponding conductive vias 312 and 332. Vias 312, 332 may be hermetic feedthroughs, for example, formed according to the teaching of aforementioned and incorporated pre-grant patent publication '524. Each of contacts 31, 33 may be coupled to a corresponding conductor of plurality of conductors 100 of lead 10 (FIG. 1).

Diaphragm portion 214 is indicated with cross-hatching in the section view of FIG. 3C, and lid portion 241 of sidewall 342 is constructed and/or supported by base portion 261 in a manner to allow discrete deformation of portion 214, in response to changes in external pressure. Although not shown in FIGS. 3B-C, a wall thickness of that area of lid portion 241 which defines diaphragm portion 214 is thinner than a remainder of lid portion 241, according to some embodiments. Methods for the manufacture of sensor 34, from the wafer level, may be found in aforementioned and incorporated references '385 and '524.

FIGS. 3B-C further illustrate a conductive layer 350 extending over an exterior surface of sidewall 342 of pressure sensor 34, in order to provide EMI shielding for capacitor 310, and an insulative layer 340 extending over conductive layer 350. Conductive layer 350 is shown coupled to ground contact 31 by conductive via 315. Although not shown, it should be understood that insulative layer 340 may be part of a bulk of insulative material, for example, silicone rubber, that fills a gap between sidewall 262 of electrode 161 and sensor 34, to isolate sensor 34 from an external implant environment of lead 10, and from electrode 161, for example, as is described in the aforementioned application Ser. No. 12/107, 987. According to the illustrated embodiment, conductive layer 350 prevents a parasitic capacitance, which exists across insulative layer 340, from significantly increasing, when pressure sensor 34 is employed within an aqueous environment of bodily fluid, and further reflects radiated EMI, and drains, via the coupling with ground contact 31, conducted EMI, thereby preventing an excess charge from building up on first electrode plate 314. Apart from layer 350, parasitic capacitance and/or charge build-up, may result in drift, or pressure errors, in measures of sensor 34. IC chip 325 may also be protected from EMI, as well as from light interference effects, by conductive layer 350. According to alternate embodiments, examples of which will be described below, additional EMI shielding may be included to augment conductive layer 350 for enhanced protection of IC chip 325 and capacitor 310. A source of EMI may be external equipment, separate from lead 10, but may more frequently be the circuit including electrodes 161 and 162 (FIG. 1), for example, when bipolar pacing pulses are conducted therethrough.

Examples of suitable materials from which conductive layer 350 may be formed, include, without limitation, titanium, platinum, nickel and tantalum or titanium alloys. Methods, which are known to those skilled in the art, for example, physical vapor deposition or electroplating, may be used to form conductive layer 350. Conductive layer 350 should be thick enough to have the minimum requisite conductivity without compromising the flexibility of diaphragm portion 214 for the desired pressure responsiveness. Such a thickness of conductive layer 350 may be upwards of 200 Angstroms and varying as appropriate; according to some embodiments, the thickness is between approximately 1 micrometer and approximately 10 micrometer.

Although FIGS. 3B-C only show a limited extent of conductive layer 350, conductive layer 350 preferably extends over almost an entirety of the exterior surface of sidewall 342 of pressure sensor 34, with just enough clearance between conductive layer 350 and supply contact 33 to keep conductive layer 350 electrically isolated from contact 33, in order to maximize EMI shielding for both IC chip 325 and capacitor 310. However, according to alternate embodiments, which will be described in greater detail, below, additional EMI shielding is provided by a separate grounded conductive sidewall, which surrounds pressure sensor 34, so that a conductive layer, such as layer 350, need only extend over an exterior surface of the diaphragm portion of the pressure sensor.

Figure 4A:
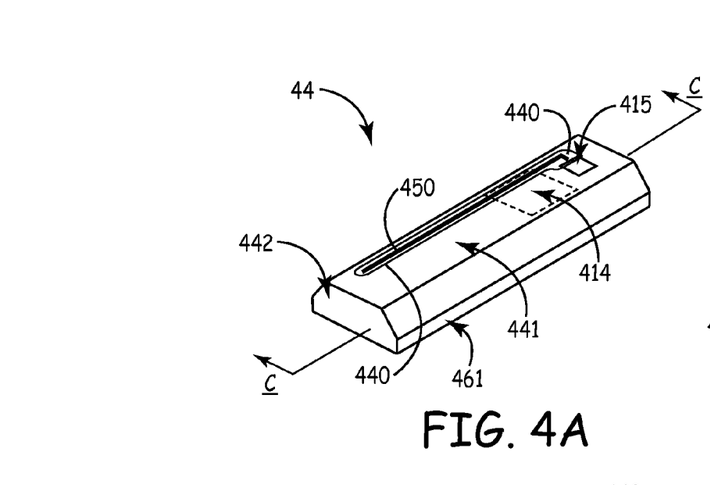
FIG. 4A is a perspective view of a pressure sensor, according to an alternate embodiment.

FIG. 4A is a perspective view of a pressure sensor 44, according to an alternate embodiment. FIG. 4A illustrates pressure sensor 44 including a capsule formed by an insulative sidewall 442, a conductive layer 450, which extends over an exterior surface of sidewall 442, and an insulative layer 440, which extends over conductive layer 450. Like sensor 34, sensor 44 may be constructed according to microelectromechanical systems (MEMS) fabrication methods, and includes a capacitive pressure transducer contained by insulative sidewall 442. Sensor 44 may be incorporated into lead 10 (FIG. 1), in the place of sensor 34 and, like sensor 34, insulative layer 440 of sensor 44 may be part of a bulk of insulative material, for example, silicone rubber, that fills a gap between sidewall 262 of electrode 161 and sensor 44, to isolate sensor 44 from an external implant environment of lead 10, and from electrode 161.

Figure 4B:
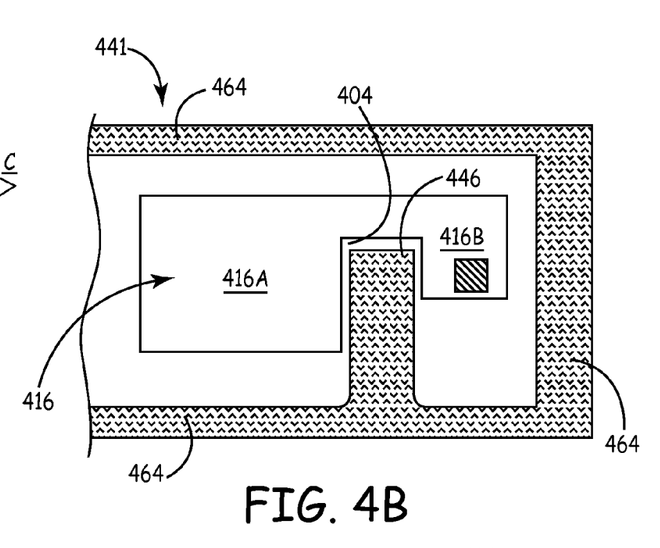
FIG. 4B is a plan view of an interior surface of a diaphragm portion of a capsule of the pressure sensor shown in FIG. 4A, according to some embodiments.
Figure 4C:
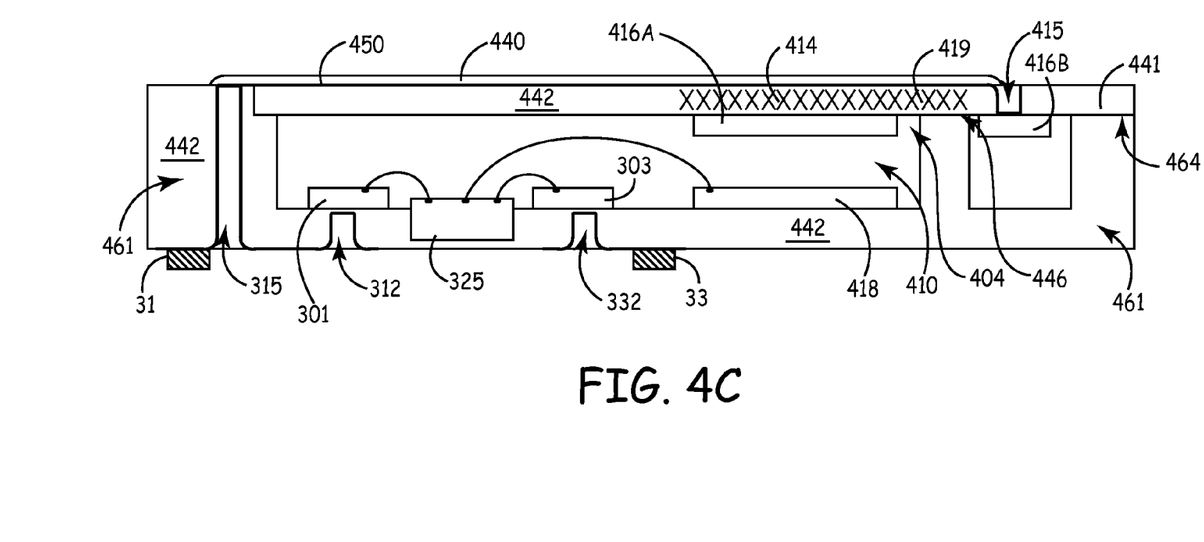
FIG. 4C is a section view, through section line C-C of FIG. 4A, according to some embodiments.

FIG. 4A further illustrates sidewall 442 including a lid portion 441 in which a diaphragm portion 414 is formed, similar to diaphragm portion 214 described for sidewall 342. FIG. 4B, which is a plan view of an opposing interior surface of lid portion 441, shows a first electrode plate 416 attached to diaphragm portion 414. With reference to FIG. 4C, which is a section view through line C-C of FIG. 4A, a second electrode plate 418 is shown attached to an interior surface of sidewall 442, spaced apart from first electrode plate 416, to form a gap capacitor 410, which is coupled to IC chip 325. Conductive layer 450, which is formed as a conductive trace, electrically couples first electrode plate 416 to ground contact 31, in order to drain away any charge that may build up on plate 416, thereby preventing drift, or pressure errors, that may otherwise result from excess charge build-up. Examples of suitable materials from which conductive layer 450 may be formed include, without limitation, gold, platinum, titanium, niobium and tantalum. A conductive via 415 couples conductive layer 450 to first electrode plate 416, and conductive layer 450 extends across diaphragm portion 414, to another conductive via 315, which couples conductive layer 450 to ground contact 31.

FIGS. 4B-C illustrate lid portion 441, of sidewall 442, including a perimeter zone 464 and a more central zone 446, which zones 464, 446 each correspond to an area of lid portion 441 that is fused to a base portion 461 of sidewall 442. FIGS. 4B-C further illustrate first electrode plate 416 including a first portion 416A and a second portion 416B, which second portion 416B is mechanically isolated from the pressure responsive movement of first portion 416A, by the fusion of lid portion 441 to base portion 461 at zone 446, so that conductive via 415, which couples electrode plate 416 to an conductive layer 450, is not subject to flex fatigue type loading.

Figure 5A:
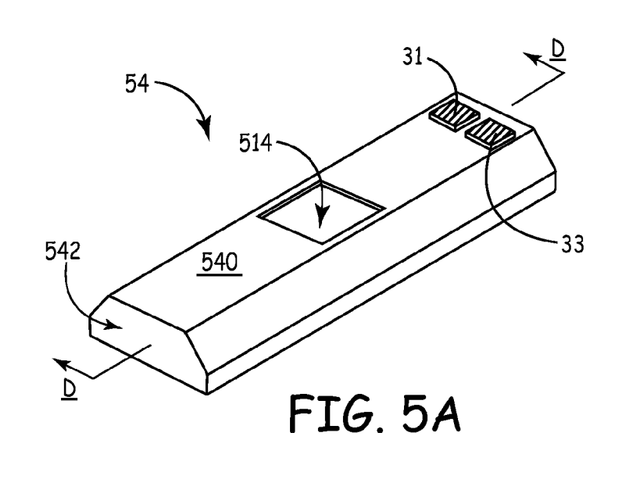
FIG. 5A is a perspective view of a pressure sensor, according to yet a further embodiment.
Figure 5B:
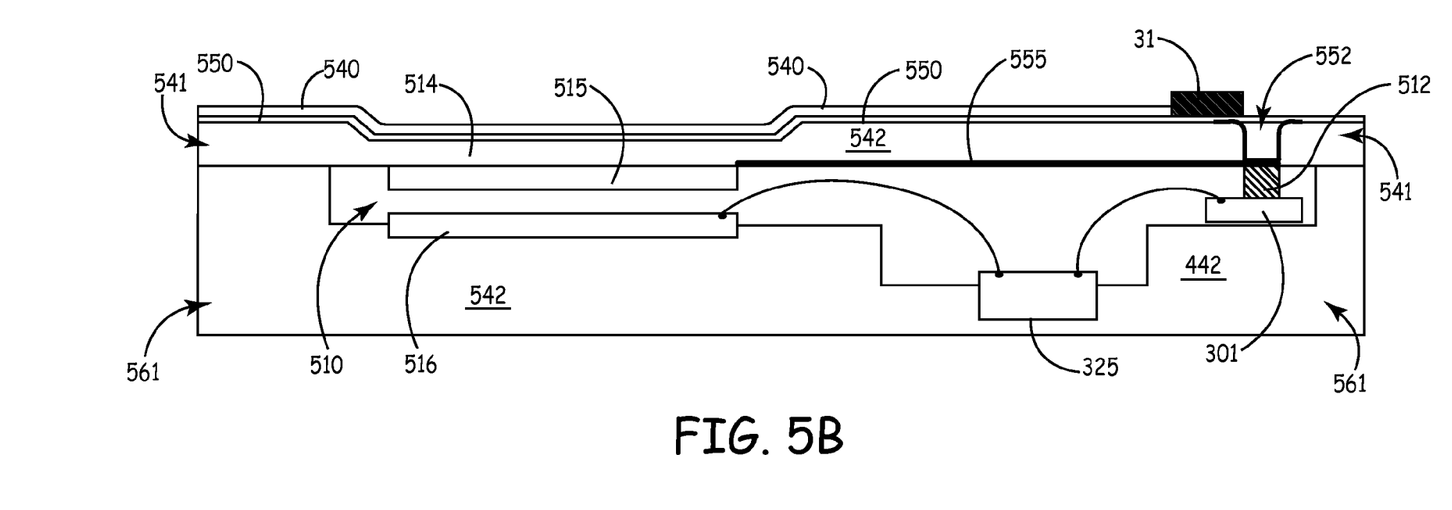
FIG. 5B is a section view, through section line D-D of FIG. 5A, according to some embodiments.

FIG. 5A is a perspective view of a pressure sensor 54, according to yet another embodiment; and FIG. 5B is a section view, through section line D-D of FIG. 5A, according to some embodiments. FIGS. 5A-B illustrate pressure sensor 54 including a capsule formed by an insulative sidewall 542, which has an exterior surface over which a conductive layer 550 extends. Pressure sensor 54 further includes an insulative layer 540, which extends over conductive layer 550. Like sensors 34, 44, sensor 54 may be constructed according to microelectromechanical systems (MEMS) fabrication methods and includes a gap capacitor 510 coupled to IC chip 325, which are both contained by insulative sidewall 542. Examples of suitable materials from which conductive layer 550 may be formed include, without limitation, those previously mentioned for conductive layer 350. Conductive layer 550 should be thick enough to have the minimum requisite conductivity with out compromising the flexibility of a diaphragm portion 514 of sidewall 542 for the desired pressure responsiveness; such a thickness may be upwards of 200 Angstroms and varying as appropriate.

In contrast to sensors 34, 44, ground contact 31 and source contact 33 of sensor 54 are located on a lid portion 541 of sidewall, as opposed to a base portion 561. A wafer-to-wafer interconnect 512, which is formed when lid portion 541 is sealed to base portion 561, is included to couple IC chip 325 to contacts 31, 33, for example, at corresponding vias (—only a via 552 for ground contact 31 may be seen in the section view of FIG. 5B). Interconnect 512 may be formed by depositing conductive materials on opposing sides of base portion 561 and lid portion 541, and then, when the opposing sides are brought together in order to seal lid portion 541 to base portion 561, the conductive materials are melted together, by local or global heating, for example, during the sealing process. Sensor 54 may be incorporated into lead 10 (FIG. 1), in the place of sensor 34 and, like sensor 34, insulative layer 540 of sensor 54 may be part of a bulk of insulative material, for example, silicone rubber, that fills a gap between sidewall 262 of electrode 161 and sensor 54, to isolate sensor 54 from an external implant environment of lead 10, and from electrode 161.

FIGS. 5A-B further illustrate diaphragm portion 514 recessed from an exterior surface of lid portion 541 of sidewall 542. A gap capacitor 510 is formed by a first electrode plate 515, which is attached to an interior surface of diaphragm portion 514, and a second electrode plate 516, which is spaced apart from first plate 515 and attached to an interior surface of base portion 561. According to the illustrated embodiment, sensor 54 includes another conductive layer 555, which extends over an interior surface of lid portion 541 to couple first electrode plate 515 to ground contact 31. Conductive layer 555 is preferably formed as conductive trace, similar to that previously described for conductive layer 450, and is coupled, through sidewall 542, by conductive via 552, to ground contact 31. Thus sensor 54 includes both grounding of electrode plate 515, by conductive layer 555, to drain away charge that may build up thereon, and an EMI shield, which is formed by conductive layer 550 extending over an exterior surface of sidewall 542. According to some embodiments, in order to further protect capacitor 510 and IC chip from EMI, layer 550 extends over almost an entirety of the exterior surface of sidewall 542, excluding a gap for electrical isolation of conductive layer 550 from contact 33. According to some alternate embodiments, for example, like those illustrated in FIGS. 5C-8B, the extent of layer 550 is more limited so that EMI shielding may need to be augmented by an additional shielding member.

Figure 5C:
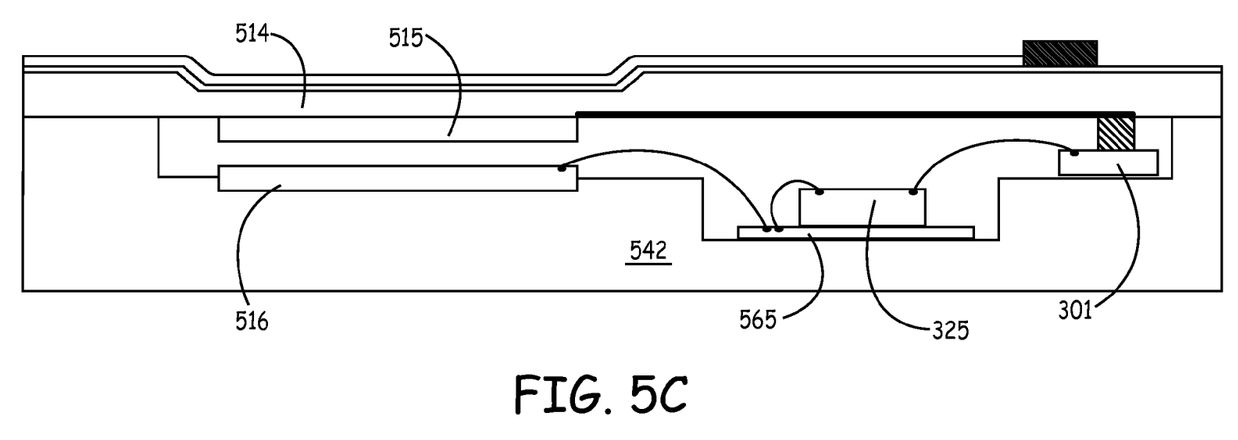
FIG. 5C is a section view, through section line D-D of FIG. 5A, according to some alternate embodiments.
Figure 5D:
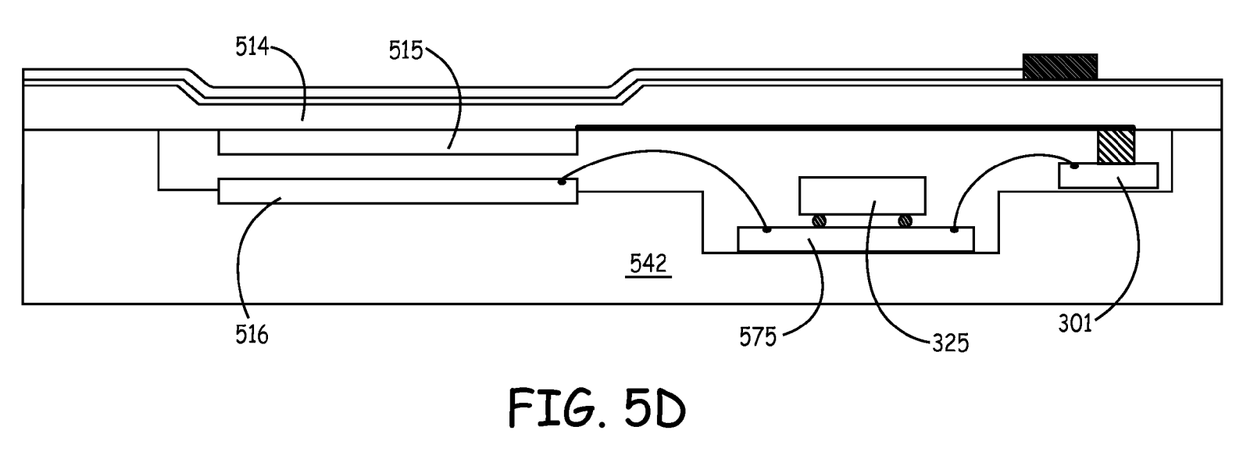
FIG. 5D is a section view, through section line D-D of FIG. 5A, according to yet further alternate embodiments.

FIG. 5C is a section view through section line D-D of FIG. 5A, according to some alternate embodiments, wherein an internal conductive layer 565 extends between sidewall 542 and IC chip 325 to act as a shield member, which provides additional EMI shielding for chip 325. Layer 565 may be formed, for example, from a solder material. Examples of suitable solder materials include, without limitation, both lead-based and lead-free solder alloys, which may be flux cored or fluxless pre-forms of the following alloys and combinations thereof: tin-based, gold-based, and indium-based. A thickness of a solder pre-form for layer 565 may be approximately 25 micrometers or approximately 50 micrometers. FIG. 5D is a section view through section line D-D of FIG. 5A, according to yet further alternate embodiments, wherein a capacitor array 575, which is coupled to IC chip 325 in a flip chip configuration, extends between sidewall 542 and IC chip 325 to act as a shield member, which provides additional EMI shielding for chip 325.

Figure 6A:
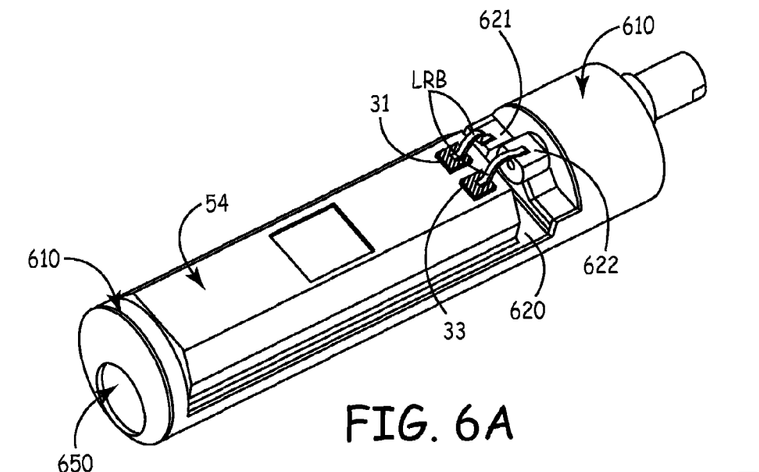
FIG. 6A is a perspective view of a subassembly including a pressure sensor mounted on a platform portion of a lead body, according to some embodiments.

FIG. 6A is a perspective view of a subassembly including pressure sensor 54 mounted on a platform portion 610 of a lead body, for example, lead body 110 (FIG. 1). Like platform portion 210, which is illustrated in FIG. 2, portion 610 includes a mounting surface 620 on which sensor 54 is mounted, for example, being adhered thereto, via adhesive bonding. Portion 610 may be separately formed, for example, molded from a relatively rigid plastic, and adapted for integration into lead body 110. According to the illustrated embodiment, sensor 54 and platform portion 610, may be inserted into electrode 161, such that conductive sidewall 262 of electrode 161 surrounds sensor 54, in the same way that sidewall 262 surrounds sensor 34, as illustrated in FIG. 1. FIG. 6A illustrates ground and source contacts 31, 33 coupled by laser ribbon bonds LRB to respective conductive inserts 621, 622. Conductive inserts 621, 622 may have been incorporated into an insulative bulk of platform portion 610 via insert molding.

Although not shown, one of the plurality of conductors 100 (FIG. 1), which extends within lead body 110, from one of connectors 14, 16, is coupled to conductive insert 621, for grounding, and another of the plurality of conductors 100, extending from the same connector, is coupled to insert 622 as a source. FIG. 6A further illustrates platform portion 610 including a by-pass lumen 650, which forms a passageway, alongside pressure sensor 54, in which another of the plurality of conductors 100 extends to couple tip electrode 162 to a contact of the other of connectors 14, 16.

Figure 6B:
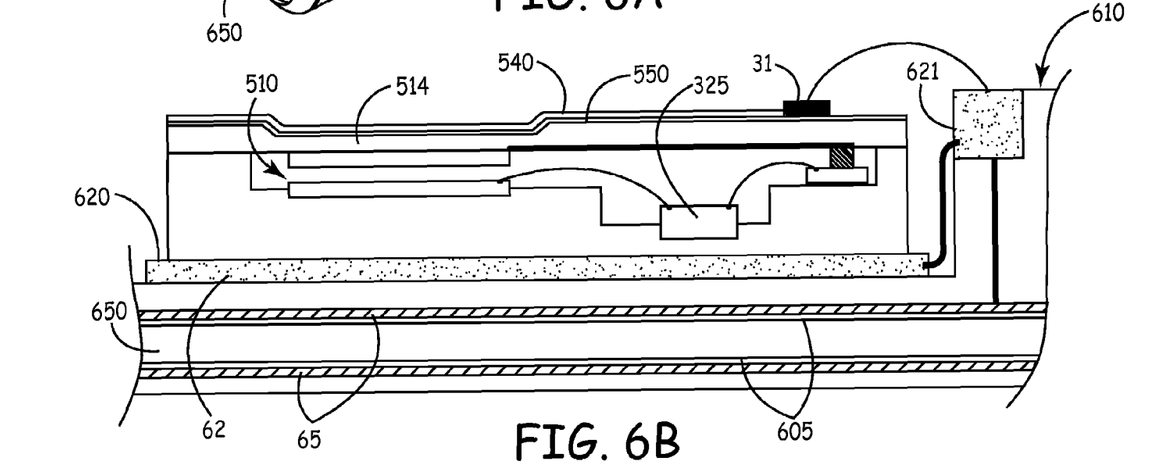
FIG. 6B is longitudinal section view of a portion of the subassembly shown in FIG. 6A, according to some embodiments.

FIG. 6B is a longitudinal section view of the subassembly shown in FIG. 6A, according to some embodiments. FIG. 6B illustrates a conductive layer 62 forming mounting surface 620 for pressure sensor 54. According to the illustrated embodiment, conductive layer 62 is grounded by a coupling with conductive insert 621, for example, via another laser ribbon bond, thereby providing additional EMI shielding for IC chip 325 and capacitor 510 of pressure sensor 54. FIG. 6B further illustrates by-pass lumen 650 including a conductive liner 65 overlaid with an insulative layer 605 to isolate liner 65 from the conductor of the plurality of conductors 100 that extends within lumen 650 when the subassembly is integrated into lead body 110 (FIG. 1). It should be noted that insulating layer 605 may not be necessary if the conductor, which extends through lumen 650, includes an outer insulative layer, or jacket. As an alternative to, or in addition to conductive layer 62, conductive liner 65 acts to provide additional EMI shielding for IC chip 325 and capacitor 510 of pressure sensor 54, being grounded by a coupling with conductive insert 621, for example, by conductive via extending within the insulative bulk of platform portion 610, as illustrated.

Figure 6C:
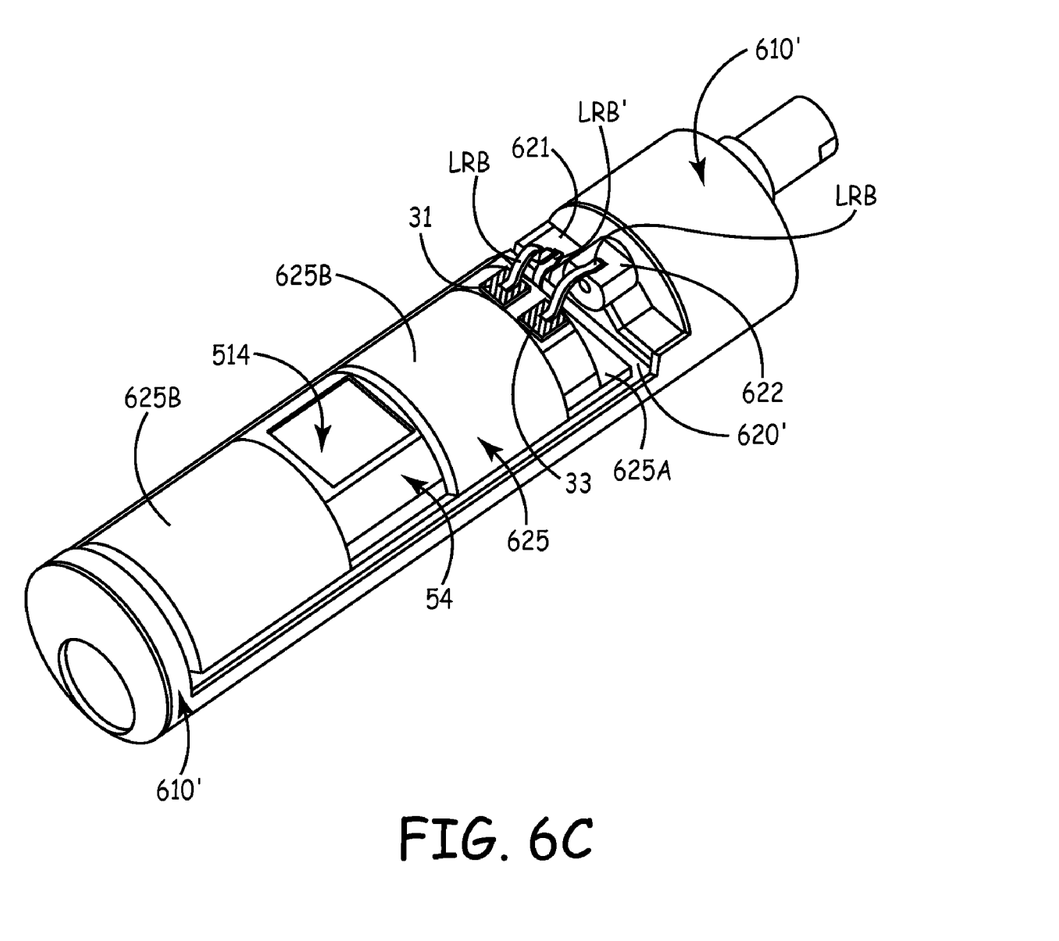
FIG. 6C is a perspective view of a subassembly including the pressure sensor mounted on a platform portion of a lead body, according to some alternate embodiments.

FIG. 6C is a perspective view of a subassembly including pressure sensor 54 mounted on a platform portion 610' of a lead body, for example, lead body 110 (FIG. 1), according to some alternate embodiments. FIG. 6C illustrates a conductive shroud 625 extending about pressure sensor 54 and including a base sidewall 625A and a pair of upper sidewalls 625B. Base sidewall 625A extends between sensor 54 and a mounting surface 620', of platform portion 610', and is grounded, via another laser ribbon bond LRB' coupling with conductive insert 621. Pair of upper sidewalls 625B extend over pressure sensor 54 and are spaced apart from one another to form an opening in order to expose diaphragm portion 514 of pressure sensor 54. According to the illustrated embodiment, and with reference back to FIGS. 5B and 6B, conductive shroud 625, along with conductive layer 550, which extends over diaphragm portion 514, provide EMI shielding for sensor 54. With further reference to FIG. 6C, shroud 625 includes another opening, located at that end which is in proximity to conductive inserts 621, 622. Pressure sensor 54 has been inserted into the other opening extends therefrom for the LRB couplings. Although not shown, when the subassembly of FIG. 6C is incorporated into a lead, such as lead 10 of FIG. 1, a bulk of insulative material, for example, silicone rubber, fills a gap between sidewall 262 of electrode 161 and conductive shroud 625, in order to isolate shroud 625 from electrode 161, and further extends between shroud 625 and portions of pressure sensor 54, in order to isolate source contact 33, conductive insert 622 and the associated LRB from the grounded components of the subassembly.

Figure 7:
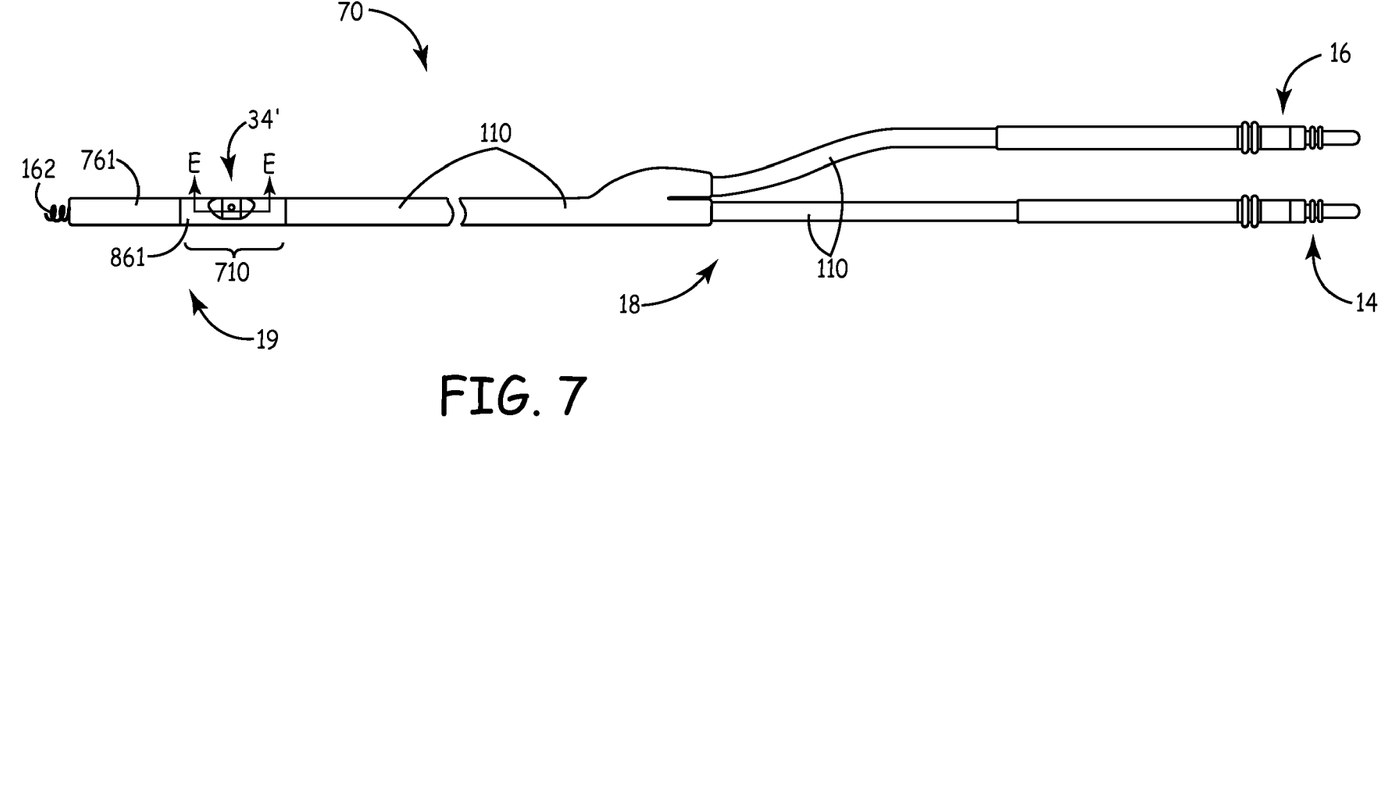
FIG. 7 is a plan view of a medical electrical lead, according to an additional embodiment.

FIG. 7 is a plan view of a medical electrical lead 70, according to another embodiment. FIG. 7 illustrates lead 70, like lead 10 of FIG. 1, including connectors 14, 16, lead body 110, and tip electrode 162. Lead 70 differs from lead 10 in that a pressure sensor 34' is included in a lead body subassembly 710 that includes a grounded conductive housing 861 rather than an electrode. Alternate embodiments of pressure sensor 34' are shown, via section views through section line E-E in FIGS. 8A-B. According to each of the embodiments illustrated in FIGS. 8A-B, housing 861, which is formed by a grounded conductive sidewall 855, for example, titanium, contains pressure sensor 34' in a cavity 810 thereof. Sidewall 855 includes an aperture 860 extending therethrough to expose diaphragm portion 214 of insulative sidewall 342 of pressure sensor 34'. Cavity 810 of housing 861, besides containing sensor 34', may contain an insulative filler material, for example, to support sensor 34' therein and/or to isolate contacts 31, 33 and their respective couplings from one another. It should be noted that sensor 34' includes gap capacitor 310 and IC chip 325, similar to sensor 34, illustrated in FIGS. 3A-C.

Figure 8A:
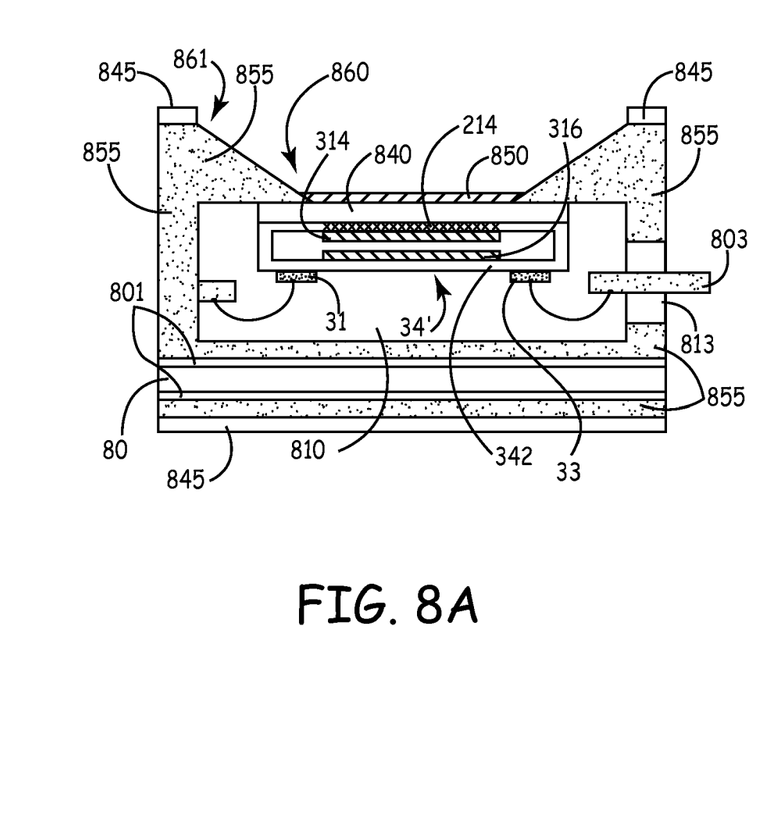
FIGS. 8A-B are section views, through section line E-E of FIG. 7, according to some alternate embodiments.
Figure 8B:
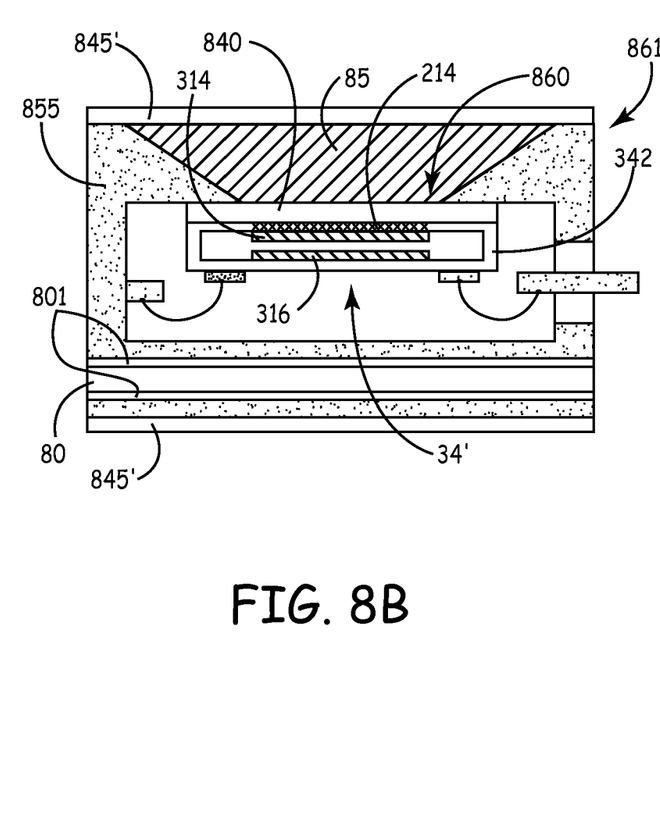

FIGS. 8A-B illustrate source contact 33 of sensor 34' coupled to a feedthrough pin 803, and ground contact 31 of sensor 34' coupled to conductive sidewall 855. According to the illustrated embodiment, feedthrough pin 803 is located for coupling to that conductor of conductors 100 (FIG. 1), which serves as the pressure sensor source conductor for lead 70, and is isolated from conductive sidewall 855 by an insulator 813, in a feedthrough configuration known to those skilled in the art. Grounded conductive sidewall 855 provides EMI shielding for IC chip 325 of sensor 34' (not shown in FIGS. 8A-B—see FIG. 3C). Sidewall 855 may be grounded via a coupling to that conductor of conductors 100, which serves as the grounded conductor for lead 70. FIGS. 8A-B further illustrate housing 861 including at least one by-pass lumen 80, through which one or more of conductors 100 may extend to couple with respective electrodes 162 and 761 (FIG. 7), which are located distal to pressure sensor 34'. Lumen 80 is shown including an insulative liner 801, which may not be necessary if the conductor(s), which extend therethrough includes an insulative outer layer, or jacket. According to alternate embodiments, lead 70 need not include one or both of electrodes 162, 761, and, if neither of electrodes 162, 761 is included on lead 70, by-pass lumen 80, of housing 861, and one of connector legs 16, 14 are not necessary.

According to the illustrated embodiments, in order to further shield pressure sensor 34' from EMI, a grounded conductive layer 850 (FIG. 8A), or 85 (FIG. 8B) spans aperture 860, which extends over diaphragm portion 214 of insulative sidewall 342 of sensor 34'. FIGS. 8A-B show layers 850, 85 grounded via contact with a perimeter of aperture 860 of grounded conductive sidewall 855.

FIG. 8A illustrates grounded conductive layer 850 extending over an insulative layer 840, which insulative layer 840 overlays diaphragm portion 214 of pressure sensor 34', and which may be an extension of the aforementioned filler material that surrounds sensor 34' within cavity 810. Examples of suitable materials from which conductive layer 850 may be formed include, without limitation, those previously mentioned for conductive layer 350. Alternatively, layer 850 may be formed from a conductive polymer material, for example, a silicone rubber filled with conductive particles, such as the electrically conductive R-2637 silicone sold by NuSil Technology. Conductive layer 850 should be thick enough to have the minimum requisite conductivity without compromising the flexibility of diaphragm portion 214 for the desired pressure responsiveness. Such a thickness of conductive layer 850 may be upwards of 200 Angstroms and varying as appropriate. FIG. 8A further illustrates an outer insulative sheath 845 surrounding housing 861, which sheath 845 may be an extension of an outer insulation of lead body 110, for example, being formed from either a silicone rubber or a polyurethane material that is commonly employed for lead body outer insulations.

FIG. 8B illustrates grounded conductive layer 85 contained within aperture 860, between insulative layer 840 and an outer insulative sheath 845', which surrounds housing 861. Like sheath 845, insulative sheath 845' may be an extension of the outer insulation of lead body 110. According to some embodiments, conductive layer 85 comprises a conductive fluid, for example, saline.

In the foregoing detailed description, the invention has been described with reference to specific embodiments. However, it may be appreciated that various modifications and changes can be made without departing from the scope of the invention as set forth in the appended claims.

The invention claimed is:
1. An implantable medical electrical lead, comprising:
a plurality of elongate conductors electrically isolated from one another;
a pressure sensor, the pressure sensor comprising:
an insulative sidewall including a pressure sensitive diaphragm portion;

a gap capacitor contained by the insulative sidewall, the gap capacitor including a first electrode plate and a second electrode plate, the first electrode plate being attached to an interior surface of the diaphragm portion of the insulative sidewall and the second electrode plate being spaced apart from the first electrode plate;

an integrated circuit contained by the insulative sidewall, the integrated circuit being coupled to the second electrode plate;

a supply contact and a ground contact, each contact being independently coupled, through the insulative sidewall, to the integrated circuit and, outside the insulative sidewall, to a corresponding conductor of the plurality of elongate conductors; and a conductive layer extending over an exterior surface of the diaphragm portion of the insulative sidewall, the conductive layer being coupled to the ground contact; and a conductive sidewall extending about the pressure sensor, the conductive sidewall including an aperture extending therethrough and being approximately aligned with the pressure sensitive diaphragm portion of the insulative sidewall of the pressure sensor.

2. The lead of claim 1, wherein the conductive sidewall is coupled to another conductor of the plurality of conductors, is isolated from the conductive layer of the pressure sensor, and forms an electrode.

3. The lead of claim 1, wherein the conductive sidewall is grounded.

4. The lead of claim 3, wherein the conductive sidewall is coupled to the ground contact of the pressure sensor and the conductive layer of the pressure sensor is coupled to the ground contact via contact with the conductive sidewall.

5. The lead of claim 4, wherein the pressure sensor further comprises an insulative layer extending between the conductive layer and the exterior surface of the diaphragm portion of the insulative sidewall.

6. The lead of claim 5, further comprising an outer insulative layer extending over the aperture of the conductive sidewall, and wherein the conductive layer of the pressure sensor comprises a conductive fluid contained between the insulative layer of the pressure sensor and the outer insulative layer.

7. The lead of claim 1, further comprising an insulative layer extending over the conductive layer of the pressure sensor.

8. The lead of claim 1, wherein the conductive layer of the pressure sensor extends over an entirety of the exterior surface of the diaphragm portion of the insulative sidewall.

9. The lead of claim 1, wherein the conductive layer of the pressure sensor extends over an entirety of the exterior surface of the diaphragm portion of the insulative sidewall, and over an exterior surface of a majority of a remainder of the insulative sidewall.

10. The lead of claim 1, wherein the pressure sensor further comprises another conductive layer extending over an interior surface of another portion of the insulative sidewall, the other portion being adjacent to the diaphragm portion of the insulative sidewall, and wherein the other conductive layer couples the first electrode plate to the ground contact.

11. The lead of claim 1, wherein the conductive layer of the pressure sensor is further coupled, by a conductive via, through the insulative sidewall, to a portion of the first electrode plate.

12. The lead of claim 11, wherein the portion of the first electrode plate is mechanically isolated from the diaphragm portion of the insulative sidewall.

13. The lead of claim 1, wherein the integrated circuit is mounted to a portion of the insulative sidewall and the pressure sensor further comprises a shield member extending between the integrated circuit and the portion of the insulative sidewall to which the integrated circuit is mounted.

14. The lead of claim 1, further comprising a lead body in which the plurality of elongate conductors extend, the lead body including a platform portion, the platform portion including a conductive surface on which the pressure sensor is mounted, the conductive surface being coupled to the conductor to which the ground contact of the pressure sensor is coupled.

15. The lead of claim 1, further comprising:

an electrode coupled to another conductor of the plurality of conductors; and a lead body in which the plurality of elongate conductors extend and to which the electrode and the pressure sensor are mounted;

wherein the electrode is mounted distal to the pressure sensor;

the lead body includes a bypass lumen through which the other conductor, which is coupled to the electrode, extends, alongside the pressure sensor; and the bypass lumen includes a conductive liner, the conductive liner being coupled to the conductor to which the ground contact of the pressure sensor is coupled and being isolated from the other conductor that extends therethrough.

16. An implantable medical electrical lead, comprising:

a plurality of elongate conductors electrically isolated from one another;

a pressure sensor, the pressure sensor comprising:

an insulative sidewall including a pressure sensitive diaphragm portion;

a gap capacitor contained within the insulative sidewall, the gap capacitor including a first electrode plate and a second electrode plate, the first electrode plate being attached to an interior surface of the diaphragm portion of the insulative sidewall and the second electrode plate being spaced apart from the first electrode plate;

an integrated circuit contained within the insulative sidewall, the integrated circuit being coupled to the second electrode plate;

a supply contact and a ground contact, each contact being independently coupled, through the insulative sidewall, to the integrated circuit and, outside the insulative sidewall, to a corresponding conductor of the plurality of elongate conductors; and a conductive layer extending over one of the interior surface and an exterior surface of the diaphragm portion of the insulative sidewall, the conductive layer being coupled to the ground contact; and an electrode including a conductive sidewall extending about the pressure sensor, the conductive sidewall including an aperture extending therethrough and being located to expose the pressure sensitive diaphragm portion of the insulative sidewall of the pressure sensor, and the electrode being coupled to another conductor of the plurality of elongate conductors.

17. The lead of claim 16, further comprising:

an insulative layer extending over the conductive layer of the pressure sensor; and wherein the conductive layer of the pressure sensor extends over the exterior surface of the diaphragm portion of the insulative sidewall.

18. The lead of claim 16, wherein the conductive layer extends over an entirety of the exterior surface of the diaphragm portion of the insulative sidewall.

19. The lead of claim 16, wherein the conductive layer extends over an entirety of the exterior surface of the diaphragm portion of the insulative sidewall, and over an exterior surface of a majority of a remainder of the insulative sidewall.

20. The lead of claim 16, wherein:
the exterior surface of the diaphragm portion of the insulative sidewall of the pressure sensor is recessed from an outer surface of the insulative sidewall; and
the conductive layer of the pressure sensor extends over the interior surface of the diaphragm portion and is coupled to the first electrode plate.

21. The lead of claim 20, wherein:
the pressure sensor further comprises another conductive layer, the other conductive layer extending over the exterior surface of the diaphragm portion of insulative sidewall; and
the other conductive layer is coupled to the ground contact.

22. The lead of claim 16, further comprising a grounded conductive shroud extending about the pressure sensor and within the conductive sidewall of the electrode, being isolated therefrom, the grounded conductive shroud including an opening that is located to expose the pressure sensitive diaphragm of the insulative sidewall of the pressure sensor.

23. An implantable pressure sensor capsule formed by an insulative sidewall, the capsule containing a gap capacitor and an integrated circuit, the gap capacitor including a first electrode plate and a second electrode plate, the second plate being spaced apart from the first plate and being coupled to the integrated circuit, the integrated circuit being coupled to a ground contact and to a supply contact, and the capsule comprising:
a pressure sensitive diaphragm forming a portion of the insulative sidewall of the capsule and including an interior surface to which the first electrode plate is attached, and an exterior surface opposite the interior surface;
a conductive layer extending over the exterior surface of the diaphragm and being coupled to the ground contact; and
an insulative layer extending over the conductive layer.

24. The capsule of claim 23, wherein the conductive layer extends over an entirety of the exterior surface of the diaphragm.

25. The capsule of claim 23, wherein the conductive layer extends over an entirety of the exterior surface of the diaphragm and over an exterior surface of a majority of a remainder of the insulative sidewall of the capsule.

26. The capsule of claim 23, further comprising another conductive layer extending over an interior surface of another portion of the insulative sidewall of the capsule, the other portion being adjacent to the diaphragm, and wherein the other conductive layer couples the first electrode plate to the ground contact.

27. The capsule of claim 23, wherein the conductive layer is further coupled, through the insulative sidewall of the capsule, to a portion of the first electrode plate.

28. The capsule of claim 27, wherein the portion of the first electrode plate is mechanically isolated from the diaphragm.

29. The capsule of claim 23, wherein the insulative layer extends over an entirety of the exterior surface of the diaphragm.

30. The capsule of claim 23, wherein the integrated circuit is mounted to a portion of the insulative sidewall, and further comprising a shield member extending between the integrated circuit and the portion of the insulative sidewall to which the integrated circuit is mounted.

31. An implantable pressure sensor capsule formed by an insulative sidewall, the capsule containing a gap capacitor and an integrated circuit, the gap capacitor including a first electrode plate and a second electrode plate, the second plate being spaced apart from the first plate and being coupled to the integrated circuit, the integrated circuit being coupled to a ground contact and to a supply contact, and the capsule comprising:
a wall segment forming a portion of the insulative sidewall, the wall segment having an interior surface and an exterior surface, the exterior surface including a recess formed therein, an area of the recess defining a pressure sensitive diaphragm portion of the wall segment, and the first electrode plate being attached to a portion of the interior surface of the wall segment, which portion is opposite the recess; and
a conductive layer coupled to the first electrode plate, the conductive layer extending from the first electrode plate, over the interior surface of the wall segment, to couple with the ground contact.

32. The capsule of claim 31, further comprising another conductive layer, the other conductive layer extending over an entirety of the exterior surface of the wall segment and being coupled to the ground contact.

33. The capsule of claim 31, wherein the integrated circuit is mounted to a portion of the insulative sidewall, and further comprising a shield member extending between the integrated circuit and the portion of the insulative sidewall to which the integrated circuit is mounted.

* * * * *